United States Patent
Mullen et al.

(10) Patent No.: US 9,254,183 B2
(45) Date of Patent: Feb. 9, 2016

(54) DENTAL IMPLANT

(75) Inventors: Lewis Mullen, Liverpool (GB); Christopher Sutcliffe, Liverpool (GB)

(73) Assignee: The University of Liverpool, Liverpool (GB)

( * ) Notice: Subject to any disclaimer, the term of this patent is extended or adjusted under 35 U.S.C. 154(b) by 1086 days.

(21) Appl. No.: 13/378,733

(22) PCT Filed: Jun. 9, 2010

(86) PCT No.: PCT/GB2010/050961
§ 371 (c)(1),
(2), (4) Date: Feb. 29, 2012

(87) PCT Pub. No.: WO2010/146383
PCT Pub. Date: Dec. 23, 2010

(65) Prior Publication Data
US 2012/0148983 A1    Jun. 14, 2012

(30) Foreign Application Priority Data
Jun. 17, 2009    (GB) .................................. 09104472

(51) Int. Cl.
| | |
|---|---|
| *B22F 3/105* | (2006.01) |
| *A61C 8/00* | (2006.01) |
| *B22F 7/00* | (2006.01) |
| *A61C 8/02* | (2006.01) |

(52) U.S. Cl.
CPC ............. *A61C 8/0012* (2013.01); *B22F 3/1055* (2013.01); *B22F 7/004* (2013.01); *A61C 8/0006* (2013.01); *A61C 8/0036* (2013.01)

(58) Field of Classification Search
None
See application file for complete search history.

(56) References Cited

U.S. PATENT DOCUMENTS

| | | |
|---|---|---|
| 4,244,689 A | 1/1981 | Ashman |
| 2002/0106611 A1 | 8/2002 | Bhaduri et al. |
| 2005/0112397 A1 | 5/2005 | Rolfe et al. |
| 2006/0147332 A1* | 7/2006 | Jones et al. ........................ 419/8 |
| 2007/0142914 A1* | 6/2007 | Jones et al. ................ 623/14.13 |
| 2009/0011384 A1 | 1/2009 | Collins et al. |
| 2009/0317762 A1* | 12/2009 | Schiefer et al. ............... 433/173 |

FOREIGN PATENT DOCUMENTS

| | | |
|---|---|---|
| EP | 1 418 013 A1 | 5/2004 |
| EP | 1 683 593 A2 | 7/2006 |
| EP | 1982672 A1 | 10/2008 |
| EP | 2002799 A1 | 12/2008 |
| SU | 1799265 A3 | 2/1993 |
| WO | WO 2004/024202 | 3/2004 |
| WO | WO 2009/004069 | 1/2009 |

OTHER PUBLICATIONS

International Search Report and Written Opinion for PCT/GB2010/050961, mailed Oct. 1, 2010; ISA/EP.

(Continued)

*Primary Examiner* — George Wyszomierski
*Assistant Examiner* — Ngoclan T Mai
(74) *Attorney, Agent, or Firm* — Harness, Dickey & Pierce, P.L.C.

(57) ABSTRACT

The present invention relates to a dental implant and to a process for fabricating the dental implant.

6 Claims, 2 Drawing Sheets

(56) References Cited

OTHER PUBLICATIONS

Mullen et al., "Selective Laser Melting: A Regular Unit Cell Approach for the Manufacture of Porous, Titanium, Bone In-Growth Constructs, Suitable for Orthopedic Applications"; Journal of Biomedical Materials Research Part B: Applied Biomaterials; Aug. 28, 2008, 11 pages.

Ngo et al., "The Osseointegration of Porous Materials Using a Rabbit Femoral Defect Model", Conference Poster (see p. 14 of the Report of the Conference Proceedings), Abstracts, Online Abstract Collection, http://asm.confex.com/asm/mpmd07/AbstractList_mpmd07.html, accessed Mar. 8, 2012.

United Kingdom Intellectual Property Office Search Report dated Oct. 12, 2009 regarding priority Application No. GB0910447.2, 9 pages.

Dental Tribune (Middle East and Africa Edition), News and Opinions, 'TiXos . . . a pioneer in the new age of implant', p. 4 Available from: http://www.leaderitalia.it/Media/LEADER97a94aGGG/PressRelease/DentalTribune_MIDD.EAST_05_08.pdf. Accessed: Sep. 10, 2009, dated: Feb. 26, 2009.

* cited by examiner

DENTAL IMPLANT

CROSS-REFERENCE TO RELATED APPLICATIONS

This application is a 371 U.S. National Stage of International Application No. PCT/GB2010/050961, filed Jun. 9, 2010, and claims priority to British patent application No. 0910447.2, filed Jun. 17, 2009, the disclosures of which are herein incorporated by reference in their entirety.

The present invention relates to a dental implant and to a process for fabricating the dental implant.

Dental implants are ordinarily based upon a screw thread design to achieve primary fixation to the host bone. The use of such solid constructs can give rise to what is known as stress shielding where there are large mismatches between the moduli of an implant and the host bone leading to bone resorption and the eventual failure of the implant.

Selective laser melting (SLM) is a process conventionally deployed for the manufacture of complex three-dimensional components from metallic, ceramic or polymeric powder feedstock. The process has been used to manufacture complex components exhibiting high density and homogeneity such as tooling dies and medical implants (see for example EP-A-1418013, EP-A-1683593 and US2007/0142914A).

The present invention seeks to provide an improved dental implant which reproduces the natural physiological loading conditions in the jaw bone whilst simultaneously achieving primary fixation via an elongate solid core.

Thus viewed from a first aspect the present invention provides a monolithic dental implant comprising:

an elongate solid core part substantially resembling a tooth root which is topologically adapted for mechanical fixation to jaw bone; and a porous exterior part capable of supporting bone in-growth.

The dental implant of the invention exploits solid mechanical fixation and porous bone in-growth to maximise short and long-term performance whilst simultaneously reducing the effects of stress shielding.

In a preferred embodiment, the elongate solid core part comprises an elongate threaded shaft which is threadedly fixatable to jaw bone. The elongate threaded shaft may be tapered or non-tapered (eg a tapered or non-tapered threaded cylindrical or conical shaft).

The elongate solid core part may comprise an elongate shaft and one or more topological retaining means such as one or more vents, slots, dimples or threads (eg single, double or triple threads). Preferably the topological retaining means is a thread (eg a helical thread).

Preferably the porous exterior part is located in at least a part (preferably a major part, particularly preferably substantially the whole) of the length of the root of the thread.

Preferably the porous exterior part is substantially helical.

Preferably the porous exterior part is radially confined by the thread. Preferably the porous exterior part is axially confined by the thread.

The elongate solid core part may terminate at a first end in a head (eg a flat or rounded head). The head may define an abutment seat in which may be seated directly or indirectly a prosthetic tooth crown. The abutment seat may be threaded.

The elongate solid core part may be tapered at a second end opposite to the first end. The elongate sold core part may terminate at the second end in a point.

The porosity of the porous exterior part is sufficient to promote bone in-growth. The porous exterior part may be partially porous. The porous exterior part may have interconnective porosity. The porosity of the porous exterior part may be regular, irregular or random. The porosity of the porous exterior part is typically in the range 60-80%.

The pore size distribution in the porous exterior part is typically in the range 80 to 800 µm, preferably 100 to 700 µm. The minimum pore size in the porous exterior part may be in the range 80 to 100 µm. The maximum pore size in the porous exterior part may be in the range 80 to 800 µm. The mean pore size in the porous exterior part is typically in the range 280 to 480 µm.

From a further patentable viewpoint the present invention seeks to exploit a selective melting technique to fabricate a dental implant as hereinbefore defined which is adapted for mechanical fixation and porous bone in-growth whilst being in a monolithic form for optimum structural integrity.

Viewed from a further aspect the present invention provides a process for fabricating a monolithic dental implant as hereinbefore defined comprising:

(a) generating a layered configuration of unit cells representative of the porous exterior part and of solid geometries representative of the elongate solid core part which together populate a three-dimensional representation of the monolithic dental implant such that each layer of the layered configuration is representative of the structural characteristics of a layer of the monolithic dental implant, wherein the layered configuration has a first layer configuration and successive layer configurations;

(b) depositing onto a platform a first layer of a biocompatible material capable of being melted by a directed energy beam;

(c) selectively melting the first layer of biocompatible material with a directed energy beam in response to the first layer configuration;

(d) for each of successive layers of biocompatible material sequentially (d1) depositing the successive layer of biocompatible material on a preceding layer of biocompatible material and (d2) selectively melting the successive layer of biocompatible material with the directed energy beam in response to a successive layer configuration and (e) allowing the first layer and each successive layer of biocompatible material to form respectively a first layer and a successive layer of the monolithic dental implant whereby to fabricate progressively the monolithic dental implant.

The directed energy beam may be a laser beam or E-beam. Preferred is a laser beam and each of steps (c) and (d2) is a step of selective laser melting (SLM).

Steps (c) and (d2) may be carried out by fusing or sintering.

Step (d1) for each successive layer may be preceded by lowering the platform. The platform may be lowered to permit deposition of successive layers in step (d1) at about 50 µm intervals.

The unit cells may be regular or irregular. The unit cells may be tetrahedral, dodecahedral, octahedral or diamond-shaped. Preferably the unit cells are octahedral. The unit cells may be space filling, interconnected or in the form of a lattice (eg a random, pseudo-random or regular lattice). The density of the unit cells may be tailored to determine the shape and extent of porosity.

The unit cells may comprise open unit cells and/or closed unit cells at the surface of the three-dimensional representation of the monolithic dental implant.

In a preferred embodiment, step (a) comprises: randomising or psuedo-randomising the unit cells. This embodiment leads to the formation of randomized structures. Due to their similarity in appearance to trabecular bone, randomized structures may aid bone in-growth and advantageously carry legacy properties that can be related back to the original unit cell on which they are based. Randomization also improves the mechanical properties of regular unit cell structures thereby resulting in improvements to both implant functionality and longevity. The degree of randomisation may be up to 30%, preferably 10 to 30%, particularly preferably 20 to 30%.

The three-dimensional representation of the monolithic dental implant may be a CAD representation manipulated into input file formats such as STereoLithography (hereafter "STL") component files. STL component file manipulation may be carried out using proprietary software such as MAGICS (Materialise, Belgium). The generation of unit cells representative of the porous exterior part in step (a) may be carried out by software such as MANIPULATOR (The University of Liverpool). The generation of solid geometries representative of the elongate solid core part in step (a) may be carried out by proprietary software.

In a preferred embodiment, step (a) comprises:

(a1) manipulating the three-dimensional representation into a first STL component file representing an exterior section and a second STL component file representing an inner solid section.

The second STL component file may represent a threaded inner solid section. Alternatively the second STL component file may represent a non-threaded inner solid section and the three-dimensional representation may be manipulated additionally into a third STL component file representing a thread.

In a preferred embodiment, step (a) comprises:

(a2) populating the exterior section represented by the first STL component file with the unit cells.

In a preferred embodiment, step (a) comprises:

(a3) slicing the inner solid section represented by the second STL component file into sliced solid geometries.

In a preferred embodiment, step (a) comprises:

(a4) merging the files generated in steps (a2) and (a3).

In steps (c) and (d2), the biocompatible material may be static or in motion. In steps (c) and (d2), the directed energy beam may be static or in motion. Preferably the source of the directed energy beam (eg laser beam) is scanned. Scanning may take place in parallel lines with beam overlap (optionally additionally with scanning in lines at an angle (eg perpendicular) to the parallel lines). Scanning may be carried out randomly. The scanning methodology may be chosen (for example) according to layer thickness. The movement of the beam is typically controlled by a galvanometer. The scanning speed is typically in the range 80 to 400 mm/s.

Preferably the biocompatible material is metal-containing. The metal-containing biocompatible material may contain one or more metal species (eg elemental metal, metal compounds, metal composites, metal alloys, metal ceramics or organometallics). Examples include stainless steel, cobalt chromium alloys, tantalum, niobium, titanium, titanium alloys and zirconia. A preferred metal-containing biocompatible material is titanium.

Typically each of steps (c) and (d2) in the process of the invention is carried out using a conventional laser. For example, the laser may be an IR (eg a near-IR) laser. The laser is typically a tunable laser.

Typically the wavelength of the directed energy beam (eg laser) is 700 nm or more, preferably in the range 700-5000 nm, particularly preferably in the range 900-1200 nm, more preferably in the range 1000-1100 nm. Each of steps (c) and (d2) may be carried out with an Ytterbium fibre laser, an E-beam Nd:YAG laser or a $CO_2$ laser.

The power output, current, exposure time, frequency, pulse repetition rate, scanning speed and focusing parameters (eg beam spot size) of the source of the directed energy beam (eg laser) may be selected by the man skilled in the art according to requirements (eg to ensure that the chemical characteristics of the biocompatible material are substantially unaltered).

The laser may be continuous or pulsed. The pulse frequency may be in the range 1 to 50 kHz.

The laser power deployed in the process of the invention may be in the range 5 to 3500 W. The beam size deployed in the process of the invention may be in the range 5 to 500 μm. The beam overlap deployed in the process of the invention may be in the range 50 to 1200%.

The thickness of the first layer and each successive layer may be in the range 5-2000 μm. Preferred is a thickness of about 50 μm.

Preferably step (e) comprises cooling the melted biocompatible material. This may occur naturally or by exposure to cooling means. The step of allowing the first layer and each successive layer of biocompatible material to form the first layer and each successive layer of the monolithic dental implant may cause adhesion.

The process of the invention may be conveniently carried out in a MCP Realizer apparatus commercially available from MCP Tolling Technologies (Stone UK) or systems manufactured by Triumph, EOS, Concept Laser GmbH and Arcam. A machine for carrying out the process of the invention is described in WO-A-2004/08398.

The present invention will now be described in a non-limitative sense with reference to an Example and to the accompanying Figures in which.

EXAMPLE

Materials and Methods

Figure 4:
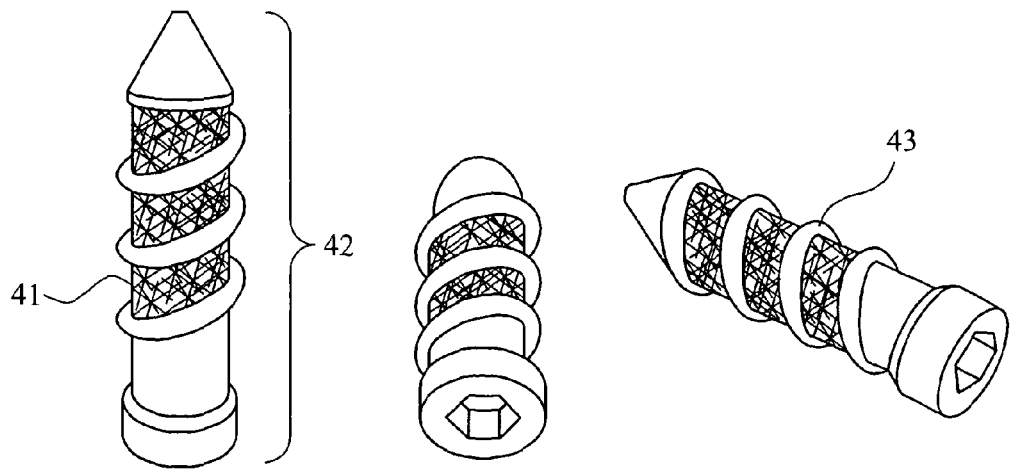
FIG. 4 illustrates the first embodiment of the dental implant of the invention fabricated by the embodiment of the process of the invention.

The present Example describes the fabrication of an embodiment of the dental implant of the invention which is illustrated in FIG. 4. The dental implant incorporates a porous exterior part (41) for bone in-growth and an elongate solid core part (42) with a thread (43) for fixation. The dental implant is fabricated monolithically using the following steps.

Step 1: Preparation of STL Component Files from a CAD File

Figure 1:
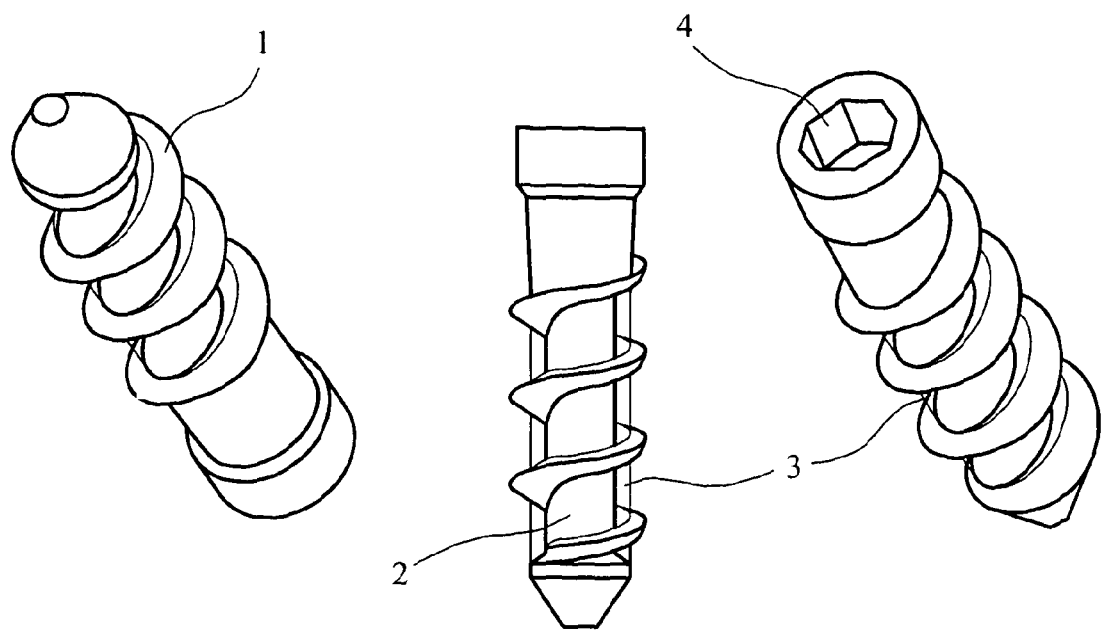
FIG. 1 illustrates a three-dimensional CAD representation of a first embodiment of the dental implant of the invention.
Figure 2:
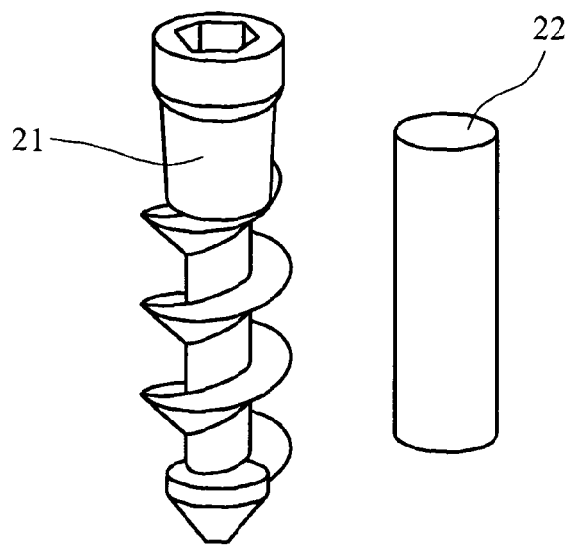
FIG. 2 illustrates STL component files used in an embodiment of the process of the invention.

A three-dimensional representation (FIG. 1) of the dental implant was modelled in two CAD files using a commercially available CAD package (Pro Engineer, PTC). The first CAD file was representative of the porous exterior part (3) and the second CAD file was representative of the elongate solid core part (1, 2). The first and second CAD files were converted into STL component files (see FIG. 2). The first STL component file (22) represented a 1.1 mm thick exterior section used to fabricate a 65% porous bone in-growth part. The second STL component file (21) represented an inner solid section including a screw thread. The STL component files were imported into proprietary software MAGICS (Materialise, Belgium), re-aligned and prepared for fabrication.

Step 2: Preparation of Bone in-Growth Part

Figure 3:
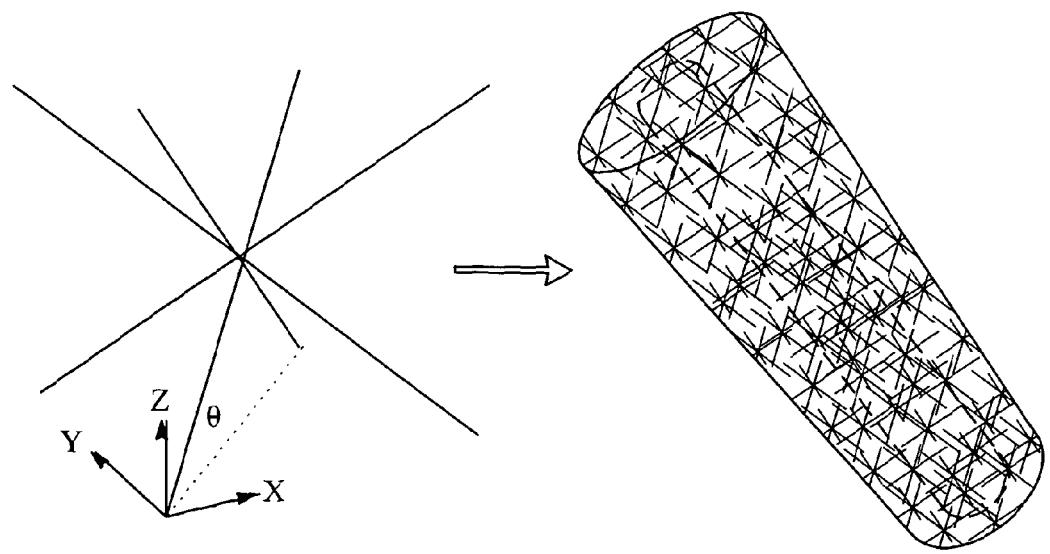
FIG. 3 illustrates the population of the exterior section by a unit cell approach in the embodiment of the process of the invention.

The volume of the exterior section represented by the first STL component file (22) was populated with a repeating unit cell using MANIPULATOR software (University of Liverpool). A single unit cell and the corresponding porous structure are shown in FIG. 3. The unit cell was a 1:1:1 aspect ratio, 600 μm, 30% randomised octahedral cell.

Step 3: Preparation of the Solid Core Part

The inner solid section represented by the second STL component file (21) was sliced into 50 μm layers and subsequently re-assembled to form a sliced file that was ready for layer fabrication.

Step 4: Selective Laser Melting

The monolithic dental implant was fabricated from commercially pure titanium (CpTi) on an MCP Realizer 2, 250 SLM machine (MCP Tooling Technologies, UK). The component files from steps 2 and 3 were loaded into the Realizer software, re-assembled and fabricated as a single part. The laser processing conditions are given in the following table:

| Parameter type | Dental implant setting |
| --- | --- |
| Powder type | Sumitomo CpTi |
| Laser power hatch (W) | 125 |
| Laser power boundary (W) | 100 |
| Laser power porous part (W) | 80 |
| Laser power solid part (W) | 125 |
| Exposure hatch (μs) | 350 |
| Exposure boundary (μs) | 300 |
| Exposure porous part (μs) | 380 |
| Exposure solid part (μs) | 350 |
| Point distance hatch (μs) | 70 |
| Point distance boundary (μs) | 70 |
| Hatch spacing (μs) | 120 |

The invention claimed is:

1. A process for fabricating a monolithic dental implant that comprises an elongate solid core part substantially resembling a tooth root which is topologically adapted for mechanical fixation to jaw bone and a porous exterior part capable of supporting bone in-growth, the process comprising:
   (a) generating a layered configuration of unit cells representative of the porous exterior part and of solid geometries representative of the elongate solid core part which together populate a three-dimensional representation of the monolithic dental implant such that each layer of the layered configuration is representative of the structural characteristics of a layer of the monolithic dental implant, wherein the layered configuration has a first layer configuration and successive layer configurations;
   (b) depositing onto a platform a first layer of a biocompatible material capable of being melted by a directed energy beam;
   (c) selectively melting the first layer of biocompatible material with a directed energy beam in response to the first layer configuration;
   (d) for each of successive layers of biocompatible material sequentially
      (d1) depositing the successive layer of biocompatible material on a preceding layer of biocompatible material and
      (d2) selectively melting the successive layer of biocompatible material with the directed energy beam in response to a successive layer configuration and
   (e) allowing the first layer and each successive layer of biocompatible material to form respectively a first layer and a successive layer of the monolithic dental implant whereby to fabricate progressively the monolithic dental implant.

2. The process as claimed in claim 1 wherein the directed energy beam is a laser beam and each of steps (c) and (d2) is a step of selective laser melting.

3. The process as claimed in claim 1 wherein the unit cells are octahedral.

4. The process as claimed in claim 1 wherein step (a) comprises: randomising or psuedo-randomising the unit cells.

5. The process as claimed in claim 1 wherein step (a) comprises:
   (a1) manipulating the three-dimensional representation into a first STL component file representing an exterior section and a second STL component file representing an inner solid section.

6. The process as claimed in claim 1 wherein step (a) comprises:
   (a2) populating an exterior section represented by a first STL component file with the unit cells;
   (a3) slicing the inner solid section represented by a second STL component file into sliced solid geometries; and
   (a4) merging the files generated in steps (a2) and (a3).

* * * * *